United States Patent [19]

Prince

[11] Patent Number: 4,769,001
[45] Date of Patent: Sep. 6, 1988

[54] METHOD AND APPARATUS FOR CALIBRATING PLURAL PUMP FLUID FLOW SYSTEM

[75] Inventor: Paul R. Prince, Fountain Valley, Calif.

[73] Assignee: Baxter International Inc., Deerfield, Ill.

[21] Appl. No.: 802,330

[22] Filed: Nov. 27, 1985

[51] Int. Cl.⁴ .............................................. A61M 1/03
[52] U.S. Cl. ........................................ 604/4; 604/67; 604/118; 604/28; 128/DIG. 13
[58] Field of Search ....................... 604/4, 5, 6, 53, 30, 604/246, 247, 80, 151, 31, 50, 65-67, 153, 118; 210/927, 97, 101, 102, 134; 137/14; 128/DIG. 13; 417/2, 5, DIG. 3

[56] References Cited

U.S. PATENT DOCUMENTS

| | | | |
|---|---|---|---|
| 3,817,658 | 6/1974 | Morase | 417/5 |
| 4,086,924 | 5/1978 | Latham . | |
| 4,197,847 | 4/1980 | Djerassi . | |
| 4,280,494 | 7/1981 | Cosgrove, Jr. et al. | 604/66 |
| 4,285,464 | 8/1981 | Latham, Sr. | 604/6 |
| 4,303,193 | 12/1981 | Latham . | |
| 4,379,452 | 4/1983 | DeVries | 604/6 |
| 4,392,849 | 7/1983 | Petre et al. | 604/66 |
| 4,416,654 | 11/1983 | Schoendorfer . | |
| 4,464,167 | 8/1984 | Schoendorfer et al. | 604/6 |
| 4,468,219 | 8/1984 | George et al. | 604/67 |
| 4,481,827 | 11/1984 | Bilstad et al. | 604/6 |
| 4,493,693 | 1/1985 | Bilstad et al. | 604/6 |
| 4,498,983 | 2/1985 | Bilstad et al. | 604/6 |
| 4,526,515 | 7/1985 | DeVries | 604/6 |
| 4,563,173 | 1/1986 | Ledley . | |
| 4,605,503 | 8/1986 | Bilstad et al. | 604/6 |
| 4,648,866 | 3/1987 | Malbrancq . | |
| 4,657,529 | 4/1987 | Prince et al. | 604/6 |

Primary Examiner—Dalton L. Truluck
Assistant Examiner—Frank Wilkens
Attorney, Agent, or Firm—Paul C. Flattery; Larry S. Nixon; Bradford R. L. Price

[57] ABSTRACT

A blood constituent processing system uses a disposable plastic fluid flow path into which an anticoagulant must be accurately metered with respect to pumped blood flow. In a preliminary calibration phase, a closed fluid flow path is provided between the anticoagulant pump and the blood pump. One of the pumps is then controlled to inject fluid into such closed path while the other pump is controlled to withdraw fluid from that path at what is nominally an equal fluid flow rate. Changes in fluid pressure within the closed fluid flow path are then monitored and the flow rate of at least one of the pumps is changed as necessary to achieve an approximately constant fluid pressure within the closed fluid flow path. The relative pump flow control required to achieve constant pressure may then be taken as a relative flow rate calibration between the two pumps so as to permit subsequent accurate pumped metering of anticoagulant into the pumped blood flow. A similar arrangement may be used to derive relative flow calibration constants for the blood pump and a packed cell pump also present in the blood constituent processing system.

30 Claims, 4 Drawing Sheets

METHOD AND APPARATUS FOR CALIBRATING PLURAL PUMP FLUID FLOW SYSTEM

This invention generally relates to method and apparatus for calibrating relative pump flow rates between plural pumps in a common fluid flow system. The invention is particularly suited for accurately calibrating relative fluid flow rates achieved by independent pumps within a disposable plastic fluid flow path of a blood constituent processing system.

Where plural independently controlled pumps are included in a common fluid flow system, it is sometimes necessary to accurately calibrate the relative flow rates between the various pumps within the system. For example, a typical blood constituent processing system may add a metered quantity of anticoagulant into a pumped flow of blood constituents. Such requirements may typically arise in a blood plasma filtering system (e.g. where whole blood is extracted from a donor, processed to remove plasma and to return the residual packed red blood cells to the donor) and/or in a platelet separation system (e.g. where whole blood from a donor is processed to remove platelets and/or plasma and the residual blood constituents are returned to the donor).

In such a blood constituent processing system, there may also be a desire to accurately calibrate the relative flow rates of the blood pumped into a filter (or other fractionating device) and the packed cells output from the filter (and/or of the filtrated or separated fraction also being output from the filter).

In such blood constituent processing systems, for obvious health reasons, the fluid flow path is typically defined by disposable plastic tubing. Such tubing may be manually inserted into conventional pulsatile pumps (e.g. where a rotating member periodically engages and compresses the tubing in a travelling wave type of motion so as to positively displace any fluid contained within the tubing in a pulsatile manner and in a direction determined by the direction of rotation), electromagnetically operated clamps (e.g. to act as "on/off" valves which controllably pinch or close off the plastic tubing at desired control points), etc. The rotational motion of each pump may be electrically monitored using hall-effect pulse generators. In one type of system, a branched section of the tubing includes a trapped compressible gas communicating with a pressure sensor so as to permit fluid pressure variations to be monitored.

Variations from one set of disposable plastic tubing to another (e.g., as further influenced by instantaneous variations in ambient temperature, pressures, flow rates, etc.) may cause significant flow variations. For example, in one exemplary system, the blood pump may experience flow variations of 10 to 15% and the anticoagulant pump may experience variations of up to approximately 10% due to variations from one set of disposable tubing to the next. At the same time, the metering ratio of anticoagulant flow to whole blood flow must typically be controlled with a greater precision to insure proper overall operation of the blood constituent processing system (e.g. for proper platelet survival).

During an initial "priming" mode of such blood constituent processing systems, it is typical to have a fluid flow path (e.g. including the anticoagulant insertion line and the whole blood extraction line) disposed between two pumps (e.g. the anticoagulant metering pump and the whole blood extraction pump) filled with liquid and including an arrangement for monitoring the fluid pressure in this fluid flow path (e.g. a trapped air or other gas or fluid column extending to a pressure sensor).

This invention provides method and apparatus for more accurately calibrating the actual fluid flow rates of the anticoagulant pump and the whole blood pump during this initial "set up" or priming mode. For example, the fluid flow path extending between the two pumps may be closed (e.g. by a hemastat or clamp temporarily placed at the juncture of the anticoagulant input tubing and the whole blood extraction tubing) so as to form a closed fluid system between the two pumps (e.g. typically filled with anticoagulant solution and a saline solution and a trapped air or gas region communicating with a pressure sensor). Both pumps may then be commanded to run at the same nominal flow rate and any resulting changes in the monitored pressure of the closed fluid flow system are then detected and used to adjust the commanded pumping rate of at least one of the pumps in a direction and by an amount required to null the value of such detected pressure changes with respect to time.

Alternatively, a change with respect to time in the liquid volume within the closed fluid system may be observed and driven to zero. In this configuration, the fluid system between the pumps need not be closed.

At the end of such calibration procedure, one will know the relative pump flow control commands required to actually achieve equal flow rates and, accordingly, this provides a relative flow rate calibration factor relating the actual flow rate of one pump to the other with a particular set of disposable plastic tubing in place.

It is also possible to use this invention to calibrate the blood pump relative to the packed cell pump in a typical plasmapheresis system where the rate of plasma filtrate extraction is determined by the difference between the pumped blood input rate and the pumped packed cell output rate. Here there is also typically an available pressure sensor located in the fluid system between these two pumps. During an initial calibration phase, the plasma filtrate output line may be temporarily clamped shut while the blood pump and packed cell pump rates are adjusted to achieve a constant average fluid pressure therebetween. The required relative pump driving rate then provides a relative fluid flow rate calibration between these two pumps.

Viewed from an overall perspective, the invention thus provides apparatus and method for deriving relative flow characteristics of plural pumps fluid-connected to a common closed fluid path by measuring the relative pump flow controls which are required to maintain an approximately constant average fluid pressure (or a constant average fluid volume) in the path while one pump is injecting fluid and the other pump is withdrawing fluid from the path. Alternatively, it may be possible in some circumstances to measure the time-based rate of pressure change in the fluid path and then to calculate or deduce the required calibration factor based on the measured rate of change. Still further, it may be possible to alternately activate the individual pumps to inject and/or to withdraw fluid from the closed path while measuring changes in fluid pressure or volume therewithin so as to deduce the relative flow characteristics of the plural pumps connected to the common closed fluid path.

These as well as other objects and advantages of the invention may be better appreciated by carefully studying the following detailed description of a presently preferred exemplary embodiment, when taken in conjunction with the accompanying drawings, of which:

Figure 1:
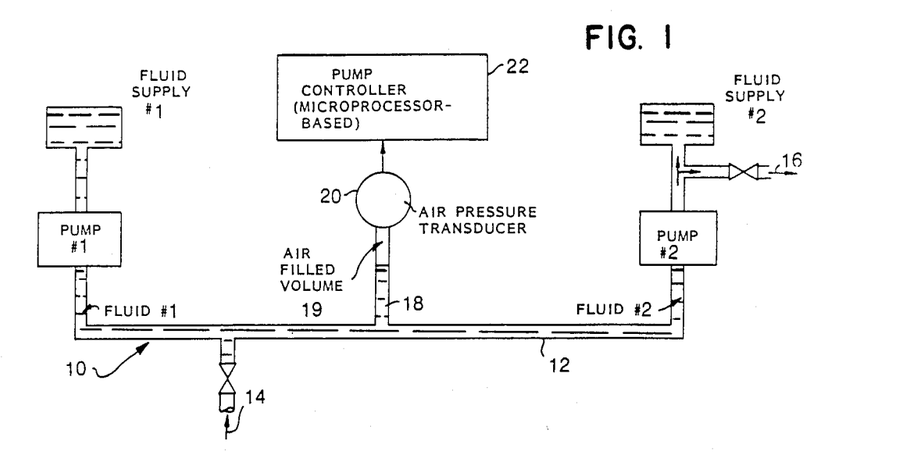
FIG. 1 is a schematic block diagram of an exemplary apparatus which may be used for practicing the method of this invention.

The system of FIG. 1 includes plural pumps (e.g. pump #1 and pump #2) interconnected by a closed fluid flow path 12 (e.g. a disposable plastic tubing as in a blood constituent processing system). In the exemplary embodiment, pump #1 and pump #2 are both peristaltic pumps of conventional design. During sustained system operation, a fluid may be input at 14 (e.g. whole blood) and mixed with a metered supply of fluid #1 (e.g. an anticoagulant solution) while being pumped onward to other portions of the apparatus at 16 (e.g. to a plasma or platelet separator/filter device, etc.) Another fluid supply #2 may also be connected with pump #2 (e.g. so as to provide a source of saline solution during initial priming mode operations or the like). A pressure measuring branch 18 of the closed fluid flow path may typically include a trapped air portion communicating with an air pressure transducer 20. An overall system controller may include a microprocessor-based pump controller 22 which is capable of independently controlling the flow rates of pump #1 and pump #2 and which also has access to pressure data derived from the air pressure transducer 20. Those in the art will recognize that there may be many other configurations of a closed fluid flow path extending between plural pumps which may be independently controlled and for which accurate relative flow rate calibration factors are desired.

In this exemplary embodiment, the relative pump flow calibration system includes a closed fluid flow path which has both incompressible liquids and compressible gases therewithin such that that gas pressure can be used to monitor pressure variations. A relative flow rate calibration of the two pumps with respect to each other is obtained by constraining the system to pump into the closed flow path with one pump and to pump out of the closed flow path with the other pump using nominally identical flow commands. If the pumps actually have equal flow rate calibration factors, then there should be a substantially constant pressure maintained within the interconnecting closed fluid flow path. By monitoring any detected pressure (or contained fluid quantity) variations within the closed fluid flow path, any calibration errors can be detected.

The hardware architecture of the microprocessor-based pump controller 22 may be of conventional design (e.g. a microprocessor chip, RAM/ROM chips, I/O chips, analog-to-digital converters, etc. conventionally interconnected). Similarly, insofar as an understanding and utilization of the present invention is concerned, the computer controlling program or software during normal system operation may be of conventional design (possibly modified so as to include a multiplicative calibration factor when generating pump control commands).

However, during a calibration period, the controller 22 also may be programmed so as to practice the method of this invention. One example of such a program is depicted in the flow chart of FIG. 2 (albeit those in the art will recognize that, in accordance with the principles of this invention as here explained, one may devise many different but suitable computer programs). A "hardwired" controller can also be readily designed to practice this invention as will also be readily appreciated by those in the art.

Figure 2:
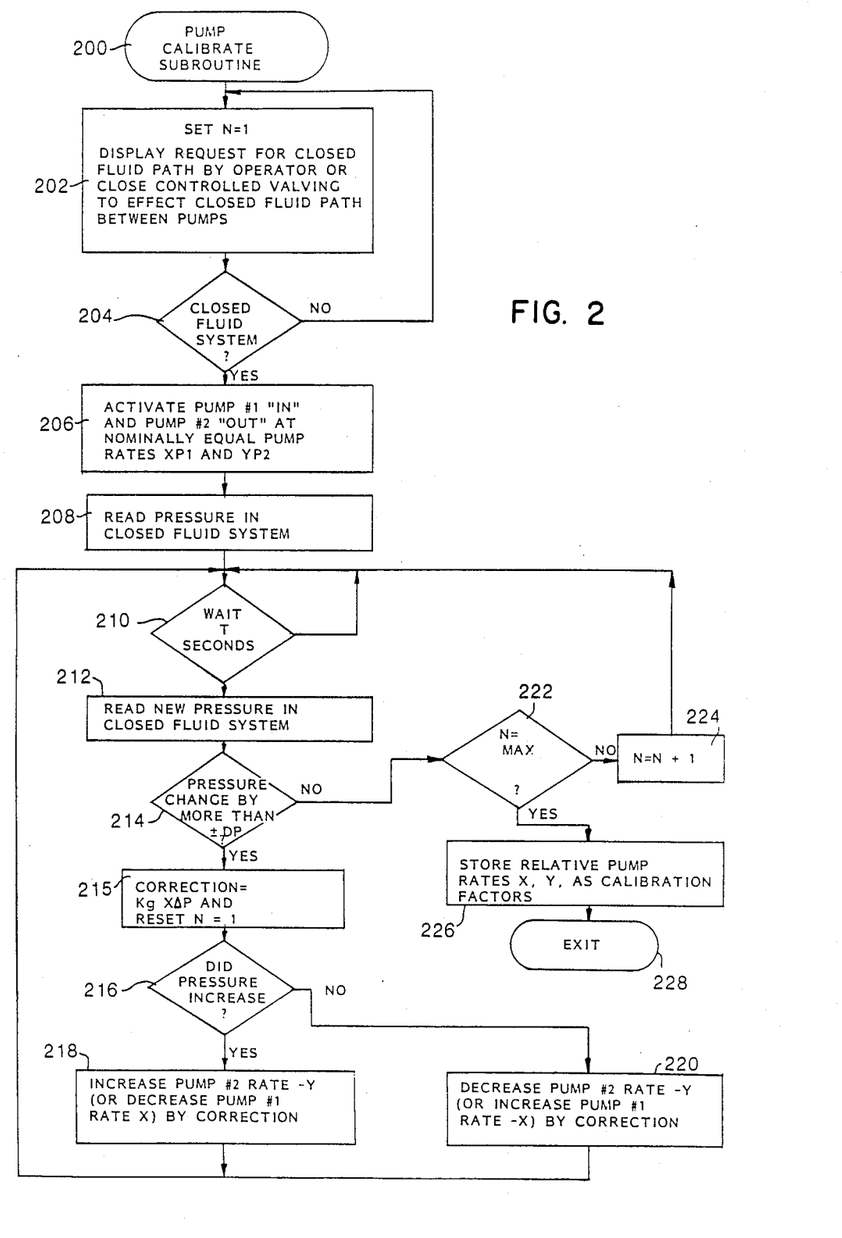
FIG. 2 is a flow diagram of a suitable computer controlling subroutine or program for the pump controller of FIG. 1.

Upon entry into the pump calibrate subroutine 200 of FIG. 2, some initial "housekeeping" details may be attended to such as those depicted at block 202. For example, a counter N may be reset to a contents of 1 and a visual operator display may be activated so as to request closure of the fluid path interconnecting the plural pumps in the system (e.g. by closing the valves near inlet 14 and outlet 16 or by applying suitable hemostats, clamps, etc.) Alternatively, if the system includes suitably placed electromagnetically controlled tubing clamps or the like, then the controller 22 may automatically close off a fluid flow path interconnecting the plural pumps in the system.

A check may be made at step 204 for the existence of a closed fluid system (e.g. by monitoring a manually activated switch and/or by performing automated stimulus/response testing routines as will be apparent). Once a properly closed fluid system is in place, control is passed to step 206 where pump #1 is activated to insert fluid into the closed system at a pump rate X while pump #2 is simultaneously activated to extract fluid from the closed system at pump rate Y—the nominal pump rates X and Y being initially selected to be equal.

A pressure reading is then taken at 208 (possibly after some finite "settling" time to permit start up of the pumps) after which a wait loop is entered at step 210 (e.g. 4.25 seconds). Upon exit from the wait loop 210, a new pressure reading is taken at 212 and tested at 214 so as to detect any pressure changes in excess of some predetermined positive or negative "noise" value. If a significant pressure change is detected, then in block 215 a correction term proportional to the error (through multiplication factor Kg) is applied, and control is passed to block 216 where it is determined whether the pressure change is in the increasing or decreasing direction. If the pressure change increased, then the pump rate Y of pump #2 is increased (or, alternatively, the pump rate X is decreased) by the correction term and control is passed back to the wait loop 210. On the other hand, if the pressure change was in the decreasing direction, then pump rate Y is decreased (or, alternatively, pump rate X is increased) by a suitable correction term and control is again passed back to the wait loop 210.

If no significant pressure change is observed, then the N counter is tested at 222 to see if it yet equals a maximum preset value corresponding to the required time interval of approximately constant pressure. If the required constant pressure period is not yet at hand, then the N counter is incremented at 224 and control is passed back to the wait loop 210. On the other hand, after a sufficiently long period of constant pressure has been detected, then exit will be made to block 226 where the then existing relative pump rates X, Y will be stored away as pump flow calibration factors and a normal exit may be made at 228 from the pump calibrate subroutine.

Figure 3:
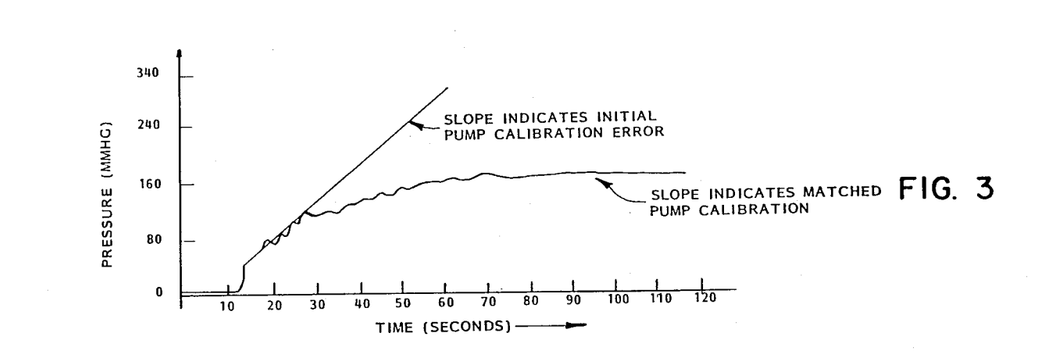
FIG. 3 is an explanatory graph depicting typical pressure changes with respect to time in the closed fluid flow path of FIG. 1.

A typical graph of pressure variations within the closed flow path as a function of time during operation of the calibration process is depicted at FIG. 3. Here, it will be seen that an initial portion of the pressure versus time curve exhibits a slope which itself indicates the relative pump calibration error. As will be understood, it may be possible to measure the value of this slope and calculate the appropriate pump flow calibration factors X, Y directly based upon such a slope measurement. However, such measurement involves some error since slope is proportional to flow rate errors and volume of trapped air 19 (see FIG. 1). After matched pump calibration has been achieved, it will be seen in FIG. 3 that the slope of the pressure versus time curve reduces to an approximately zero value.

Figure 4:
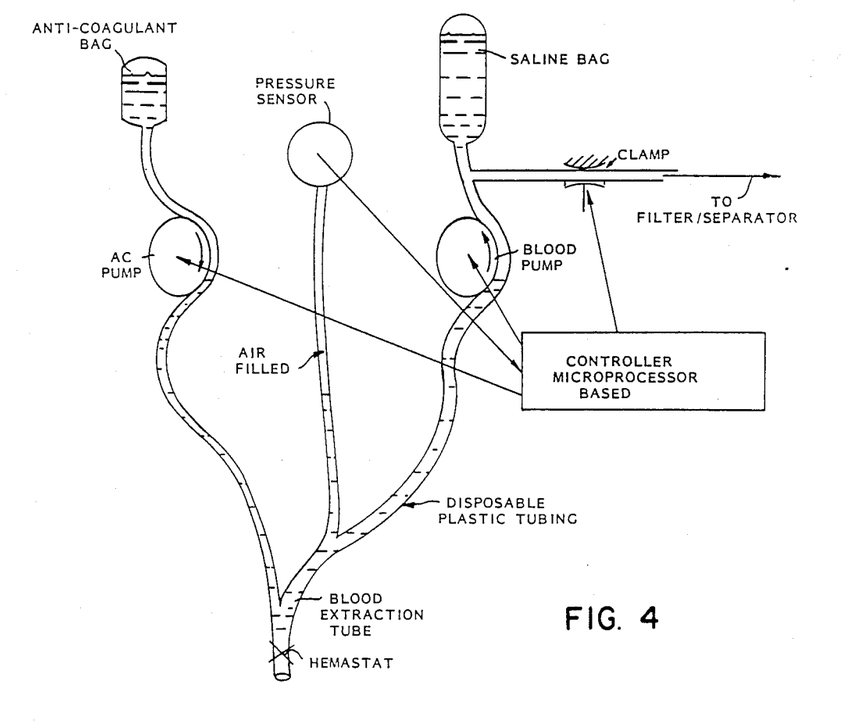
FIG. 4 is a schematic depiction of a portion of a blood constituent processing system which embodies a closed fluid flow path between two independently controlled pumps in a manner which is similar to that depicted in FIG. 1.

FIG. 4 is similar to FIG. 1 but more realistically depicts a portion of a typical blood constituent processing system and a portion of a typical disposable plastic tubing harness which is typically threaded into various pumping, clamping, pressure sensing, etc. apparatus which is, in turn, under control of a microprocessor-based controller. During a priming mode, the fluid flow path between the anticoagulant pump and the blood pump is filled with liquid (thereby trapping a quantity of air in a pressure measuring branch of the tubing communicating with the pressure sensor). A hemostat or clamp is then placed at the junction of the anticoagulant tubing and of the blood extraction tubing so that the two liquids (anticoagulant solution and saline solution in this preliminary priming mode) form a closed system between the two pumps, with the air region and pressure sensor monitoring the closed system.

Pressure then builds up or falls as the two pumps are commanded to produce the same nominal flow rate. A control system such as that depicted in FIG. 5 automatically observes the pressure changes over a time period and responsively controls at least one of the pumps to change its actual flow rate. As previously mentioned, the necessary calibration factor relating the relative actual flow rates of the pumps with a given disposable plastic tubing harness in place may be obtained by measuring the slope or rate of change of the pressure versus time curve and/or by empirically modifying the relative pump calibration factors so as to null any detected pressure changes. For example, a modified pump flow constant may be generated so as to direct one of the pumps actually to rotate faster or slower for a specified nominal liquid flow rate. After sufficient precision has been attained, the calibration procedure is complete.

Figure 5:
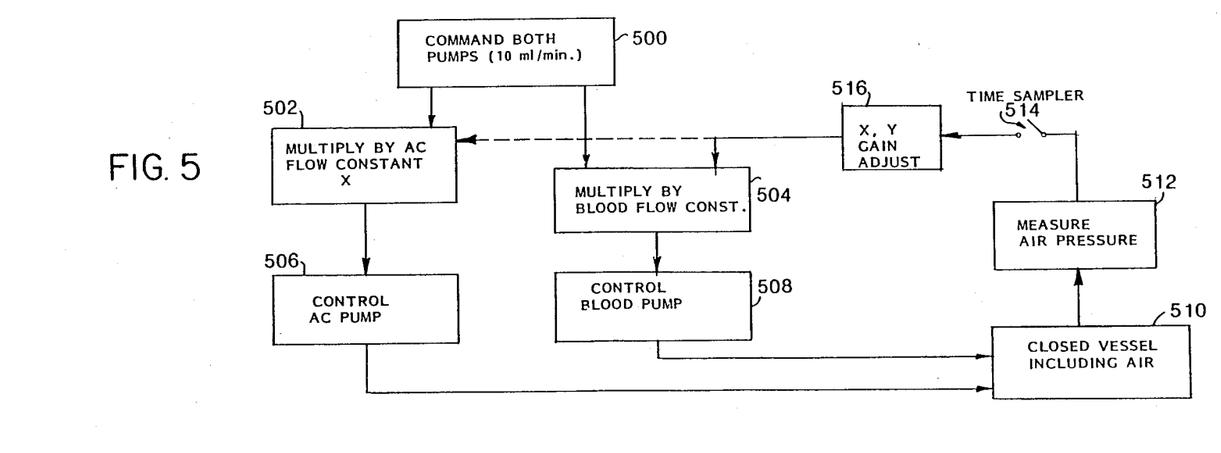
FIG. 5 is a schematic block diagram of a control system which may be suitable for use as the controller in the apparatus of FIGS. 1 and/or 4.

In one exemplary embodiment, as depicted in FIG. 5, both pumps are initially commanded to flow at a rate of 10 milliliters per minute as represented schematically at block 500 in FIG. 5. This command is multiplied by an anticoagulant pump flow constant or calibration factor X at block 502 and by a blood pump flow constant or calibration factor Y at block 504 before actually being used to control the speed of the anticoagulant pump at block 506 and the blood pump at 508. The two pumps then act upon the closed fluid vessel system (including air) as depicted at block 510 and cause an air pressure response which is measured at block 512. A timed sampler 514 then feeds a gain adjustment control block 516 where the calibration factors X, Y are adjusted relative to one another so as to correct for any noted pump flow rate errors.

Figure 6:
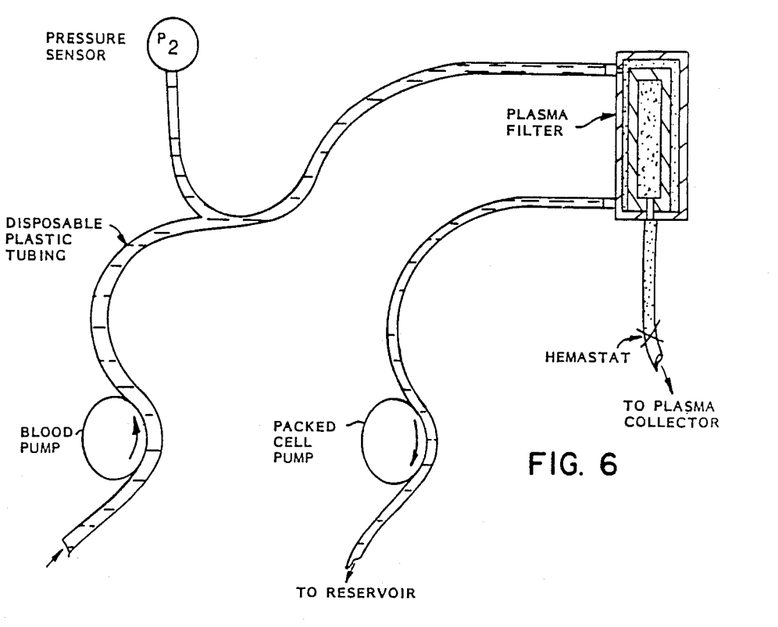
FIG. 6 is similar to FIG. 4 but depicts a different portion of a blood constituent processing system where a blood pump and a packed cell pump are flow calibrated relative to one another.

Another portion of a typical blood constituent processing system is depicted in FIG. 6. Here the disposable plastic tubing extends on the output side of the blood pump to a plasma filter and on to a pumped packed cell output flow from the filter. In operation, the flow rate of plasma filtrate (e.g., 6 ml/min) may be determined by controlling the pumped rate of blood input (e.g., 50 ml/min) relative to the pumped rate of packed cell output (e.g., 44 ml/min). As in the FIG. 4 embodiment, a branch of tubing between the two pumps includes a volume of trapped air communicating with a pressure transducer. After the system is filled with liquid, the blood pump may be operated near the expected rate of use (or perhaps initially slower) while the plasma filtrate output is clamped shut and the packed cell pump is operated at a nominally equal rate. The pressure P2 will begin to rise or fall due to any difference in actual pump rates. That compliance due to the air pocket in the tubing to the pressure transducer keeps the pressures within reasonable bounds for initial errors in flow rates. Typically, this calibration procedure may be performed after some initial filtration has occurred and blood plasma has already filled the plasma filter and tubing down to the clamp point on the plasma output tube.

Figure 7:
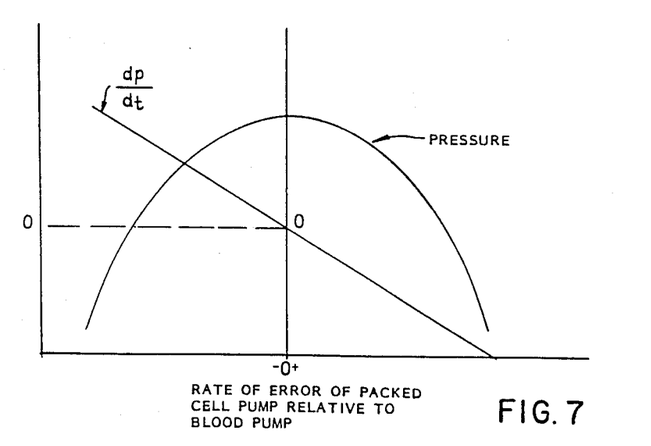
FIG. 7 is a graphical depiction of pressure changes versus pump flow error rate.

FIG. 7 illustrates the resulting pressure profile and its first derivative (with respect to time) for a regularly changing relative difference in pump flow rates. An iterative or other procedure may then be employed (as before) to determine relative pump flow rate calibration factors which may thereafter be used to achieve accurate relative pump flow rates. Following such measurement, the relative flow rates can be temporarily shifted to bring the pressure within a normal range (e.g., as measured just prior to plasma clamp closure) before re-opening the plasma clamp.

As will now be appreciated, if one of the pumps can also be calibrated with respect to an absolute standard (e.g., if the packed cell pump delivers its output to a collection reservoir which is carried by an electronic weighing or other volume/mass/weight measuring device), then one can, in turn, use the relative pump flow calibration factors to derive absolute calibration factors for the other pump(s).

If pulsatile pumps are employed, there will, of course, be periodic pressure/volume pulses which may be disregarded (e.g., by employing suitable low pass "averaging" filters) in the calibration procedures.

While only a few exemplary embodiments have been explained in detail, those skilled in the art will recognize that many modifications and variations may be made in these exemplary embodiments while yet maintaining many of the novel features and advantages of this invention. Accordingly, all such modifications and variations are to be included within the scope of the appended claims.

What is claimed is:

1. A method for automatically deriving relative flow calibration data of plural pumps connected with a common fluid path therebetween, said method comprising the steps of:
   automatically controlling said pumps to inject fluid into said common fluid path and/or to withdraw fluid from said common fluid pathat respectively associated nominal rates;
   automatically measuring changes in at least one fluid flow parameter occurring within said common fluid path in response to said controlling of said pumps at said respectively associated nominal rates; and
   automatically deriving relative flow calibration data for the individual pumps using said measured changes is obtained.

2. A method as in claim 1 wherein said controlling step comprises controlling a first pump to inject fluid into said path at a first nominal rate and controlling a second pump to withdraw fluid from said path at a second nominal rate, at least one of said rates being controlled to maintain an approximately constant fluid pressure in said path.

3. A method as in claim 1 wherein said controlling step comprises controlling a first pump to inject fluid into said path at a first nominal rate and controlling a second pump to withdraw fluid from said path at a second nominal rate, at least one of said rates being controlled to maintain an approximately constant fluid volume in said path.

4. A method as in claim 1 wherein:
   said controlling step comprises controlling a first pump to inject fluid into said path at a first nominal rate and controlling a second pump to withdraw fluid from said path at a second nominal rate; and
   said measuring step comprises measuring the rate-of-change in fluid pressure in said path.

5. A method for deriving relative flow calibration data for plural pumps connected with a common fluid path, said method comprising the step of:
   measuring the relative pump flow controls which are required to maintain an approoxiamtely constant fluid pressure in said path while one pump is injecting fluid into said path and another pump is withdrawing fluid from said path.

6. A method for deriving relative flow calibration data for plural pumps connected with a common fluid path, said method comprising the step of:
   measuring the relative pump flow controls which are required to maintain an approximately constant fluid volume in said path while one pump is injecting fluid into said path and another pump is withdrawing fluid from said path.

7. A method for deriving relative flow calibration data for an anticoagulant pump and a blood pump connected in a blood constituent processing system with a disposable plastic tubing which includes a common fluid path, said method comprising the steps of:
   installing a disposable plastic tubing into a blood constituent processing system and providing a common closed fluid path within the disposable tubing and extending between an anticoagulant pump and a blood pump;
   controlling the pumps to inject and/or withdraw fluid from said path at respective nominal rates;
   measuring a predetermined fluid parameter in said path during said controlling step; and
   deriving said relative flow characteristics in response to the controlling and/or measuring steps.

8. A method as in claim 7 wherein said controlling step comprises simultaneously (a) controlling a first pump to inject fluid into said path at a first nominal rate, (b) controlling a second pump to withdraw fluid from said path at a second nominal rate, and (c) changing at least one of said controlled nominal rates so as to maintain an approximately constant measured fluid pressure or volume in said path.

9. A method as in claim 8 wherein said deriving step comprises recording the relationship between the nominal pump flow rates required to maintain said approximately constant fluid pressure.

10. A method as in claim 7 wherein said deriving step comprises measuring the time-based rate of pressure change in said path.

11. A method for obtaining a relative flow calibration factor for a system of plural pumps connected with a common fluid flow path, said method comprising:
   controlling at least two of the pumps to simultaneously inject and withdraw fluid from said path at relative rates which approximately maintain a constant fluid pressure or volume within said path; and
   measuring at least one relative pump flow calibration factor for said at least two pumps based on the controlled pumping rates required to approximately maintain said constant fluid pressure or volume.

12. A method for calibrating relative pump flow rates of plural pumps connected with a common fluid-containing structure, said method comprising:
   controlling at least one of said pumps to pump liquid into said structure at a first nominal rate;
   simultaneously controlling at least one other of said pumps to pump liquid out of said structure at a second nominal rate;
   monitoring the fluid pressure or volume within said structure during said controlling step; and
   adjusting at least one of said nominal pump rates in response to said monitored fluid pressure or volume so as to obtain calibration data representing calibrated relative pump flow rates between plural pumps.

13. A method for calibrating a first pump flow with respect to a second pump flow in a blood constituent processing system, said method comprising the steps of:
   installing a disposable plastic tubing into said blood constituent processing system which includes a common fluid flow path between said first pump and said second pump;
   pumping fluid into said path with one of said pumps at a first predetermined nominal rate and pumping fluid out of said path with the other of said pumps at a second predetermined nominal rate, which rates are initially set to be at assumed equal values;
   detecting changes in fluid pressure or volume within said path caused by said pumping step;
   adjusting at least one of said first and second rates in response to said detecting step so as to maintain an approximately constant fluid pressure or volume within said path; and
   deriving a relative pump flow calibration factor based on the controlled nominal flow rates required by said adjusting step.

14. Apparatus for deriving relative flow calibration data for plural pumps connected with a common fluid path, said apparatus comprising:

means for controlling said pumps to inject fluid into said path and/or to withdraw fluid from said path at respectively associated nominal rates;

means for measuring changes in at least one fluid flow parameter occuring within said path in response to said injection of fluid into, and withdrawal of fluid from, said common fluid path; and means for deriving relative flow calibration data for the individual pumps in response to said measured changes.

15. Apparatus as in claim 14 wherein said means for controlling controls a first pump to inject fluid into said path at a first nominal rate and controls a second pump to withdraw fluid from said path at a second nominal rate which is controlled to maintain an approximately constant fluid pressure or volume in said path.

16. Apparatus as in claim 14 wherein:

said means for controlling controls a first pump to inject fluid into said path at a first nominal rate and controls a second pump to withdraw fluid from said path at a second nominal rate; and said means for measuring measures the rate-of-change in fluid pressure or volume in said path.

17. Apparatus for deriving relative flow calibration data of plural pumps connected with a common closed fluid path, said apparatus comprising:

means for independently controlling plural pumps connected with a common closed flow path; and means for measuring the relative pump flow controls which are required to maintain an approximately constant fluid pressure or volume in said path while one pump is injecting fluid into said path and another pump is withdrawing fluid from said path.

18. Apparatus for deriving relative flow calibration data of first and second pumps connected in a blood constituent processing system with a disposable plastic tubing which includes a common fluid path between said pumps, said apparatus comprising:

a disposable plastic tubing disposed in a blood constituent processing system and providing a common closed fluid path within the disposable tubing and extending between said first pump and said second pump;

means for controlling the pumps to inject and/or withdraw fluid from said path at respective nominal rates;

means for measuring a predetermined fluid parameter in said path; and means for deriving said relative flow calibration data in response to the effected pump control and/or the measured parameter.

19. Apparatus as in claim 18 wherein said means for controlling simultaneously (a) controls a first pump to inject fluid into said path at a first nominal rate, (b) controls a second pump to withdraw fluid from said path at a second nominal rate, and (c) changes at least one of said controlled nominal rates in response to said means for measuring so as to maintain an approximately constant measured fluid pressure in said path.

20. Apparatus as in claim 19 wherein said means for deriving records the relationship between the nominal pump flow rates required to maintain said approximately constant fluid pressure.

21. Apparatus as in claim 18 wherein said means for deriving measures the time-based rate of pressure change in said path.

22. Apparatus comprising:

a system of plural pumps connected with a common fluid flow path;

means for controlling at least two of the pumps to simultaneously inject and withdraw fluid from said path at relative rates which approximately maintain a constant fluid pressure or volume within said path; and means for measuring at least one relative pump flow calibration factor for said at least two pumps based on the controlled pumping rates required to approximately maintain said constant fluid pressure or volume.

23. Apparatus comprising:

plural pumps connected with a common fluid-containing volume;

means for controlling at least one of said pumps to pump liquid into said volume at a first nominal rate;

means for simultaneously controlling at least one other of said pumps to pump liquid out of said volume at a second nominal rate;

means for monitoring the fluid pressure or volume within said volume during said controlling step; and means for adjusting at least one of said nominal pump rates in response to said monitored fluid pressure or volume so as to obtain calibrated relative pump flow rates between plural pumps.

24. Apparatus for calibrating, during a preliminary set-up period, anticoagulant pump flow with respect to blood pump flow in a blood constituent processing system, said apparatus comprising:

disposable plastic tubing located in a blood constituent process system which includes a closed fluid flow path between an anticoagulant pump connected to a source of anticoagulant solution and a blood pump connected to a source of saline solution;

means for pumping fluid into said path with one of said pumps at a first predetermined nominal rate and pumping fluid out of said path with the other of said pumps at a second predetermined nominal rate, which rates are initially set to be at assumed equal values;

means for detecting changes in fluid pressure within said path caused by said pumping;

means for adjusting at least one of said first and second rates in response to said detected changes so as to maintain an approximately constant fluid pressure within said path; and means for deriving a relative pump flow calibration factor based on the controlled nominal flow rates required by said means for adjusting.

25. A method for automatically deriving relative flow calibration data for plural pumps connected with a common fluid path therebetween and a normally open fluid path which establishes fluid communication between the common fluid path and a fluid source, said method comprising:

establishing a closed fluid path which includes said common fluid path by terminating, during a preliminary set-up period, fluid communication between said common fluid path and said fluid source;

automaticallly controlling said pumps, during said preliminary set-up period, to inject fluid into said common fluid path and/or to withdraw fluid from said common fluid path at respectively associated nominal pumping rates;

automatically measuring changes in at least one fluid flow parameter occuring within said closed common fluid path in response to said controlling of said pumps at said respectively associated nominal rates; and automatically deriving said relative flow calibration data for the individual pumps in response to said measured changes.

26. A method of operating a fluid system of the type having plural pumps connected with a common fluid path therebetween and a normally open fluid path which establishes fluid communication between the common fluid path and a fluid source, said method comprising:
 (a) deriving relative flow calibration data for said plural pumps by:
  (i) establishing a closed fluid path which includes said common fluid path by terminating, during a preliminary set-up period, fluid communication between said common fluid path and said fluid source;
  (ii) automatically controlling said pumps, during said preliminary set-up period, to inject fluid into said common fluid path and/or to wtihdraw fluid from said common fluid path at respectively associated nominal pumping rates;
  (iii) automatically measuring changes in at least one fluid flow parameter occuring within said closed common fluid path in response to said controlling of said pumps at said respectively associated nominal rate; and
  (iv) automatically deriving said relative flow calibration data for the individual pumps in response to said measured changes; and then
 (b) reestablishing, during a normal operating cycle after said preliminary set-up period, said normally open fluid path and controlling the operating rates of said plural pumps based upon said derived relative flow calibration data.

27. Apparatus for automatically deriving relative flow calibration data of plural pumps connected with a common fluid path therebetween and a normally open fluid path which establishes fluid communication between the common fluid path and a fluid source, said apparatus comprising:
 means for establishing a closed fluid path which includes said common fluid path by terminating, during a preliminary set-up period, fluid communication between said common fluid path and said fluid source;
 means for automatically controlling said pumps, during said preliminary set-up period, to inject fluid into said common fluid path and/or to withdraw fluid from said common fluid path ar respectively associated nominal pumping rates;
 means for automatically measuring changes in at least one fluid flow parameter occurring within said closed common fluid path in response to said controlling of said pumps at said respectively associated nominal rates; and
 means for automatically deriving said relative flow calibration data for the individual pumps in response to said measured changes.

28. A method for automatically deriving relative flow calibration data of plural pumps connected with a common fluid path therebetween, said method comprising the steps of:
 automatically controlling said pumps to inject fluid into said common fluid path and/or to withdraw from said common fluid path at respectively associated nominal pumping rates;
 automatically measuring changes in at least one fluid flow parameter occurring within said common fluid path in response to said controlling step of said pumps at said respectively associated nominal rates;
 comparing said measured changes in said at least one flow parameter to a predetermined standard value for said flow parameter;
 automatically continually modifying the pumping rate of at least one of said pumps from said nominal pumping rate thereof in response to said measured changes being at variance with said predetermined standard value until said measured changes are comparable to said predetermined standard value; and
 automatically deriving relative calibration data representative of said modified pumping rate of said at least one pump relative to said respective nominal rate thereof, whereby calibration data for the individual pumps using said measured changes is obtained.

29. A method for deriving a relative flow calibration data for plural pumps connected with a common fluid path, said method comprising the steps of:
 (a) operating said pumps at respective nominal pumping rate such that one pump injects fluid into said path and another pump withdraws fluid from said path;
 (b) measuring changes of at least one fluid flow parameter occurring within said common fluid path during said operation of said pumps at said respective nominal pumping rates and determining whether said measured changes are within a predetermined value which is required to maintain an approximately constant fluid pressure in said path while said one pump is injecting fluid into said path and said another pump is withdrawing fluid from said path;
 (c) modifying the pumping rate of said one and/or another pumps from said nominal pumping rate thereof until said changes of said at least one fluid flow parameter meausured according to step (b) is within said predetermined value; and
 (d) deriving a calibration value for said one and/or another pumps which is representative of said modified pumping rate, whereby calibration data for said pumps is obtained.

30. Apparatus for deriving relative flow calibration data for plural pumps connected with a common fluid path, said apparatus comprising:
 means for controlling said pumps to inject fluid into said path and/or to withdraw fluid from said path at respectively associated nominal rates;
 means for measuring changes in at least one fluid flow parameter occuring within said path in response to said injection of fluid into and withdrawal of fluid from said common fluid path; and
 means for deriving relative flow calibration data for the individual pumps, said means for deriving including;
  (i) means for comparing said measured changes in said at least one flow paratmeter to a predetermined standard value for said flow parameter;

(ii) means for automatically continually modifying the pumping rate of at least one of said pumps from said nominal pumping rate thereof in response to said measured changes being at variance with said predetermined standard value until said measured changes are comparable to said predetermined standard value; and (iii) means for generating a calibration value representative of said modified pumping rate of said at least one pump relative to said respective nominal rate thereof, whereby calibration data for the individual pumps using said measured changes is obtained.

* * * * *